United States Patent [19]

Binder

[11] Patent Number: 5,057,437

[45] Date of Patent: Oct. 15, 1991

[54] METHOD FOR BROAD SPECTRUM DRUG DETECTION

[75] Inventor: Steven R. Binder, Berkeley, Calif.

[73] Assignee: Bio-Rad Laboratories, Inc., Hercules, Calif.

[21] Appl. No.: 225,108

[22] Filed: Jul. 27, 1988

[51] Int. Cl.$^5$ ............................................. G01N 30/02
[52] U.S. Cl. ..................................... 436/161; 436/178; 436/815; 436/901; 210/656; 210/198.2
[58] Field of Search ..................... 210/635, 656, 198.2, 210/659; 436/161, 178, 815, 816, 901

[56] References Cited

U.S. PATENT DOCUMENTS

| | | | |
|---|---|---|---|
| 3,625,652 | 12/1971 | Fujimoto et al. | 23/230 B |
| 3,901,655 | 8/1975 | Shukla et al. | 436/901 X |
| 4,056,468 | 11/1977 | Breiter et al. | 210/31 R |
| 4,204,952 | 5/1980 | Snyder | 210/659 |
| 4,680,120 | 7/1987 | Ramsden et al. | 436/901 X |
| 4,740,306 | 4/1988 | Litwack et al. | 210/635 X |

FOREIGN PATENT DOCUMENTS

| | | |
|---|---|---|
| 0177344 | 9/1986 | European Pat. Off. |
| 0215432 | 3/1987 | European Pat. Off. |
| 3002996 | 1/1980 | Fed. Rep. of Germany |

OTHER PUBLICATIONS

M. Kelner et al., "Reversed-Phase Liquid-Chromatographic Simultaneous Analysis for Thiopental and Pentobarbital in Serum," *Clinical Chemistry*, vol. 29, No. 6, pp. 1097-1100 (1983).

C. G. Fletterick et al., "Liquid-Chromatographic Determination of Acetaminophen in Serum," *Clinical Chemistry*, vol. 25, No. 3, pp. 409-412 (1979).

B. A. Robinson et al., "Liquid-Chromatographic Determination of Aminoglutethimide in Plasma," *Clinical Chemistry*, vol. 29, No. 6, pp. 1104-1105 (1983).

C. D. Scott et al., "Use of Sequential Columns of Microreticular and Pellicular Ion-Exchange Resins in the High-Resolution Separation of Complex Biochemical Mixtures," *Journal of Chromatography*, vol. 83, pp. 383-393 (1973).

K. Ogan et al., "Analysis of Complex Samples by Coupled-Column Chromatography," *Analytical Chemistry*, vol. 54, No. 2, pp. 169-173 (1982).

R. N. Gupta et al., "Liquid-Chromatographic Determination of Nadolol in Plasma," *Clinical Chemistry*, vol. 29, No. 6, pp. 1085-1087 (1983).

Slais, K., et al., "Screening of Amphetamines by Gradient Microbore Liquid Chromatography and Precolumn Technology," *J. Chromatography* 393 (1987): 57-68.

LeCaillon, J.-P., et al., "Influence of Solute Polarity in Column-Switching Chromatography for the Assay of Drugs in Plasma and Urine," *J. Chromatography* 317 (1984): 493-506.

Bidlingmeyer, B. A., et al., "Separation of Organic Amine Compounds on Silica Gel with Reversed-Phase Eluents," *Anal. Chem.* 54 (1982): 442-447.

Bidlingmeyer, B. A., et al., "Determination of Tricyclic Antidepressants Using Silica Gel with a Reversed-Phase Eluent," *Chromatographia*, 15(2) (1982): 83-85.

(List continued on next page.)

Primary Examiner—David L. Lacey
Assistant Examiner—Jeffrey R. Snay
Attorney, Agent, or Firm—Townsend and Townsend

[57] ABSTRACT

Biological fluid test samples are analyzed for a broad spectrum of drugs, including benzodiazepines, amphetamines, tricyclic antidepressants and opiates, in a single isocratic analysis using a chromatographic column system containing three analytical columns—an anion exchange column, a reversed phase column and a cation exchange column. A pre-column is also included to purge the sample of salts, proteins, peptides and hydrophilic anions. Carrier liquids containing acetonitrile at various strengths are used for distribution of the various drugs among the columns, elution of the drugs from the columns, and column purging and conditioning. The system readily lends itself to automation, automatic periodic sampling, and component identification and quantification.

26 Claims, 1 Drawing Sheet

OTHER PUBLICATIONS

Richardson, et al., "Bare Silica as a Reverse-Phase Stationary Phase: Liquid Chromatographic Separation of Antihistamines with Buffered Aqueous Organic Mobile Phases," *J. Pharm. Sci.* 73(10) (1984): 1480–1482.

Snyder, L. R. et al., "Boxcar Chromatography-a New Approach to Increased Analysis Rate and Very Large Column Plate Numbers," *J. Chromatography* 203 (1981): 3–17.

Harbin, D. N. et al., "The Identification of Drugs of Abuse in Urine Using Reverse Phase High Pressure Liquid Chromatography," *J. Liquid Chromatography* 3(2) (1980): 243–256.

Adamovics, J., et al., "Preparative Liquid Chromatography of Pharmaceuticals Using Silica Gel with Aqueous Eluents," *J. Liquid Chromatography* 9(1) (1986): 141–155.

Adamovics, J. A., "Determination of Antibiotics and Antimicrobial Agents in Human Serum by Direct Injection onto Silica Liquid Chromatographic Columns," *J. Pharm. Biomed. Anal.* 5(3) (1987): 267–274.

Wheals, B. B., "Isocratic Multi-Column High-Performance Liquid Chromatography as a Technique for Qualitative Analysis and its Application to the Characterization of Basic Drugs Using an Aqueous Methanol Solvent," *J. Chromatography* 187 (1980): 65–85.

Hill, D. W. et al., "HPLC Photodiode Array UV Detection for Toxicological Drug Analysis,"*J. Liquid Chromatography* 10(2&3) (1987): 377–409.

Hill, D. W., et al., "Computerized Library Search Routine for Comparing Ultraviolet Spectra of Drugs Separated by High-Performance Liquid Chromatography," *Anal. Chem.* 59 (1987): 350–353.

Little, C. J., et al., "Applications for a Microprocessor-Controlled Valve-Switching Unit for Automated Sample Cleanup and Trace Enrichment in High-Performance Liquid Chromatography," *J. Chromatography* 264 (1983): 183–196.

Gluckman, J. C. et al., "Transitory Mobile Phase Environments for Rapid Selectivity Changes in Liquid Chromatography: Application to Organic Dyestuffs," *Anal. Chem.* 59 (1987): 79–85.

Mura, P., et al., "Screening Procedure for Benzodiazepines in Biological Fluids by High-Performance Liquid Chromatography Using a Rapid-Scanning Multichannel Detector," *J. Chromatography* 416 (1987): 303–310.

Riedmann, M., et al., "Automated Serum Sample Analysis Use Cleanup Column In-Line," *American Clinical Products Review,* Apr. 1986: 8–15.

De Jong, J., et al., "Selective On-Line Sample Handling for the Determination of Barbiturates in Urine by Liquid Chromatography with Precolumn Technology," *J. Chromatography* 381 (1986): 431–437.

Ishii, D., et al., "Studies of Micro High-Performance Liquid Chromatography. IV. Application of the Micro Precolumn Method to the Analysis of Corticosteroids in Serum," *J. Chromatography* 156 (1978): 173–180.

Sonnefield, W. J., et al., "On-Line Multidimensional Liquid Chromatographic Determination of Polynuclear Aromatic Hydrocarbons in Complex Samples," *Anal. Chem.* 54 (1982): 723–727.

Erni, F., et al., "Application of Column Switching in High-Performance Liquid Chromatography to on-Line Sample Preparation for Complex Separations," *J. Chromatography* 204 (1981): 65–76.

Nielen, M. W. F., "Fully Automated Sample Handling System for Liquid Chromatography Based on Precolumn Technology and Automated Cartridge Exchange," *J. Chromatography* 393 (1987): 69–83.

Lingeman, H., et al., "High-Performance Liquid Chromatographic Analysis of Basic Compounds on Non-Modified Silica Gel and Aluminum Oxide With Aqueous Solvent Mixtures," *J. Chromatography* 352 (1986): 261–274.

Schmid, R. W., et al., "Use of Unmodified Silica With Buffered Aqueous Mobile Phase Mixtures for Selective Chromatography of Basic Drugs," *Chromatographia* 24 (1987): 713–719.

Demorest, D. M. et al., "Library Search Using an HPLC Diode-Array Detector," *LC-GC* 5(2): 128–142.

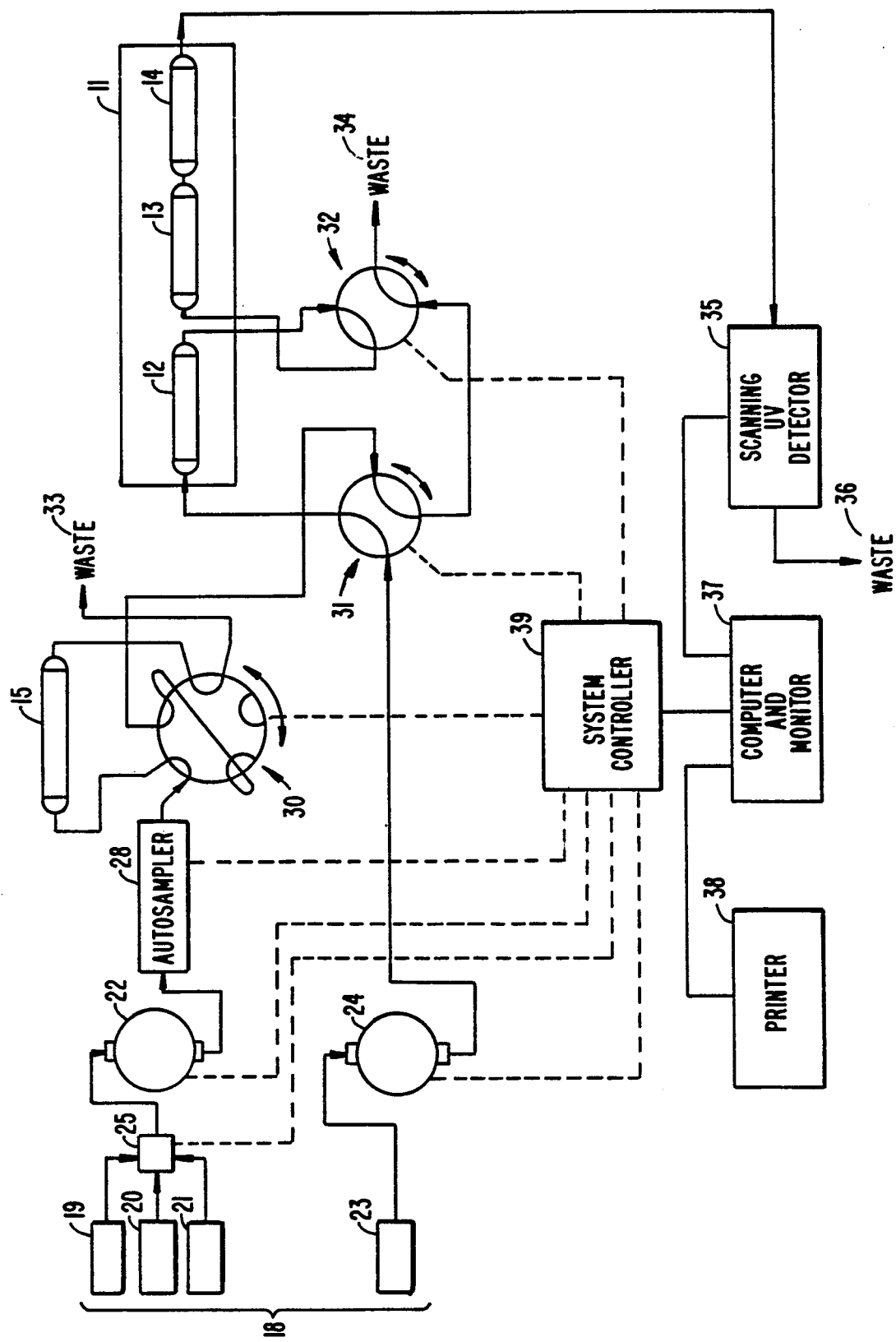
FIGURE

METHOD FOR BROAD SPECTRUM DRUG DETECTION

BACKGROUND OF THE INVENTION

This invention relates to analytical systems and methods for biological fluids such as serum and urine. In particular. this invention relates to chromatographic systems for multiple drug analyses in biological fluids.

A wide range of analytical methods are known for the detection of toxic drugs in serum or urine. The most common techniques are those involving immunological interactions and those involving chromatographic separation. Immunological techniques directed at single species can provide highly accurate information regarding the presence and amount of the species in question. When a single immunological assay is used for multiple drug detection. it will generally detect only drugs of a particular class, and will not provide identification of the specific drugs which are present or their concentrations. Chromatographic techniques, including thin-layer chromatography, high performance liquid chromatography and gas chromatography, may permit detection of a multitude of drugs at the same time, but generally require extensive sample preparation and a total analysis time of 1-2 hours. Neither immunological nor chromatographic techniques as presently known are useful for rapidly analyzing wide ranges of drugs.

SUMMARY OF THE INVENTION

The present invention provides a chromatographic graphic system and method which combines several unique features permitting a broad spectrum drug analysis by isocratic separation in an unusually short period of time.

Among the unique features of the invention are a distinct combination and arrangement of analytical columns, notably an anion exchange column, a reversed phase column, and a cation exchange column arranged sequentially in that order. The invention further provides the unique combination of these analytical columns with a pre-column. Samples to be analyzed are passed initially through the pre-column to be purged of components not sought to be detected in the analysis. Still further, the invention provides an automated system which combines detection and scanning elements with a library of known spectra and retention times, to identify and quantify each component as it emerges from the column system fully separated from the other drugs originally present in the test sample. Still further, the invention provides a system which combines column reconditioning features with its chromatographic functions so that portions of the system may be reconditioned or regenerated for subsequent test samples while other portions of the system are in use performing the separation of a sample already injected. The invention further provides for the automatic injection of a multitude of test samples in sequence. with full system regeneration and conditioning in between each sample.

By virtue of these unique features, the invention provides for the analysis of any liquid test sample to identify and quantify a large majority of the several hundred most frequently prescribed drugs, as well as all drugs commonly analyzed by liquid chromatography. In particular, the system provides a highly specific separation and detection of four classes of basic drugs—benzodiazepines, amphetamines, tricyclic antidepressants and opiates—while grouping these drugs according to class. The system further provides for the separation and detection of additional drugs of various types, including antihistamines, phenothiazines and barbiturates. As indicated above, the system lends itself well to automation, and as a result, full analyses can be obtained unattended in an unusually short period of time—substantially less than 1 hour, and in many cases on the order of 15 minutes.

Further unique and unusual features of the invention, together with further advantages and utilities, will be apparent from the description which follows.

BRIEF DESCRIPTION OF THE DRAWING

The attached figure is a block flow diagram of a drug detection system in accordance with the invention.

DETAILED DESCRIPTION OF THE INVENTION AND PREFERRED EMBODIMENTS

The separation media used in the present invention are placed in a column arrangement in such a manner that separations of certain classes of drugs are performed primarily on a single column. In particular, the system is arranged such that the anion exchange medium selectively retains hydrophobic anions and a major portion of neutral compounds, while the separation of benzodiazepines (and other weak bases) and hydrophobic bases and neutrals occurs on the reversed phase column. The cation exchange column provides for the separation of all basic compounds, including further separation of those separated on the reversed phase column.

To further categorize these columns and how they are used, the anion exchange column is selected and used in such a manner that it causes substantially no retention of either bases or very hydrophilic neutral compounds, although a slight retention of weak bases (benzodiazepines) is permissible. The separation of barbiturates and other weak acids occurs on this column.

The reversed phase column is selected and used in such a manner as to cause substantially no retention of hydrophilic bases, barbiturates or other anions including those which may have passed through the anion exchange medium without retention.

Likewise, the cation exchange column is selected and used in such a manner that there is substantially no retention of anions and barbiturates. A slight retention of neutral compounds is permissible in this column.

The anion exchange medium is preferably a polymeric resin having quaternary ammonium functional sites. A particularly effective polymer is styrenedivinylbenzene, and the functional sites are preferably tetra(-lower alkyl) ammonium moieties. A product which is particularly effective and commercially available as of the filing date of this specification is AMINEX ® A-28 resin, supplied by Bio-Rad Laboratories, Hercules, Calif., which is an HPLC grade strongly basic anion exchange resin, with tetramethylammonium functional groups on an 8% cross-linked styrene-divinylbenzene matrix, with an average particle size of about 11 microns.

The reversed phase column may be a derivatized silica. preferably one bearing alkyl functional groups. Alkyl groups of choice are those containing alkyl chains of 6 carbon atoms or more, preferably from about 6 to about 18. In particularly preferred embodiments, the functional groups are attached by bonding the silica to a dimethylalkylsilane, in which the alkyl group is that referred to above. Silicas of this description are readily commercially available. In further preferred embodiments, the carbon loading of the silica, i.e., the carbon atom content in weight percent, ranges from about 6% to about 12% with about 8% to about 10% especially preferred. A commercially available product which has been found to be effective is MOS-HYPERSIL ®, a dimethyloctylsilane bonded to silica with a carbon loading of 9%, obtained from Shandon Scientific Ltd., distributed by Keystone Scientific, State College, Pa. The average particle size is approximately 5 microns and average pore size is approximately 120 Angstroms. For bonded silicas in general for this application, pore sizes of 50 to 120 Angstroms may be used.

A typical cation exchange medium is underivatized silica, widely available commercially. One example of a commercial product effective for this medium is ADSORBOSPHERE ®, available from Alltech Associates, Deerfield, Ill., consisting of an underivatized silica with an average particle size of 5 microns, a pore size ranging from 50 to 80 Angstroms, and a surface area exceeding 350 m$^2$/g.

By selection of the lengths of each of these columns, one can minimize or substantially eliminate interference between emerging peaks, and minimize the analysis time as well. In general, and particularly with the preferred column packings described above, minimal peak interference is achieved with an anion exchange column ranging from about 10 mm to about 30 mm in length, a reversed phase column of about 10 mm to about 50 mm in length, and a cation exchange column of about 100 mm to about 250 mm in length.

The precolumn may be a polymeric resin of hydrophobic character. A preferred example is styrenedivinylbenzene, although other resins of similar character may be used. Resins of this type are widely available commercially, one example being a product designated PRP-1, a hydrophobic styrene-divinylbenzene copolymer having a particle size of 12-20 microns, available from Hamilton Co., Reno, Nev. Typical column lengths range from about 10 mm to about 30 mm.

Test samples may be applied to the precolumn by a buffer solution having a pH of 7.5 or greater, preferably from about 7.5 to about 9.0. One example of such a buffer system is an aqueous solution containing potassium borate at about 0.03% to about 0.3% by weight, and preferably is a 0.1% aqueous solution of potassium borate with a pH of approximately 8.0. This buffer solution may be used as a carrier solution to apply the samples to the column, and also as a purging solution to purge the column once the sample is applied, to remove from the sample those species whose detection by the system is not desired. This may be achieved by passing excess buffer solution through the sample-impregnated column, preferably in both directions. Species removed include inorganic salts, proteins, peptides and hydrophilic anions.

For chromatographic separations in the analytical columns, a carrier liquid containing acetonitrile is used as the mobile phase. The acetonitrile content may vary, and will generally fall within the range of about 10% to about 50% by volume. Higher acetonitrile concentrations within this range are effective to move components through the columns more rapidly than lower concentrations. For example, concentrations of about 40% by volume or above may be used to dislodge the components from the precolumn after the purging of unwanted species has been completed. Concentrations on the order of 35%. 30% and lower may likewise be used on the analytical columns to separate the drugs within each of the various classes. Carrier liquids similar to these but with acetonitrile concentrations higher than the above-indicated range are effective as wash solutions to recondition the columns after use and to thereby prepare them for the next sample.

Preferred carrier liquids contain additional agents for controlling the retention and/or selectivity of certain drug classes on particular columns, either to enhance separation or to shorten elution times. In particular, long chain alkylamines, preferably those having carbon chains of 6 carbons or greater, may be used to accelerate the elution of certain classes such as tricyclic antidepressants from the reversed phase column. A particularly effective example is dimethyl octyl amine. The concentration of this additive may vary, but will generally fall within the range of about 0.001% to about 0.05% (volume basis), with preferred amount within the range of about 30 to about 300 microliters per liter of carrier liquid.

Likewise, retention time and selectivity on the cation exchange column may be controlled by inclusion of a quaternary amine in the carrier liquid. Again, concentrations may vary, although the amount will generally fall within the range of about 0.002M to about 0.05M. Typical quaternary amines are tetraalkylammonium hydroxides and halides. Examples are tetrabutylammonium hydroxide, tetraethylammonium hydroxide, and tetramethylammonium chloride. In preferred embodiments, the concentration ranges from about 0.1 to about 2.0 grams per liter of carrier liquid.

The carrier liquid also preferably includes a water-soluble organic solvent combined with an aqueous buffer solution. The pH is preferably from about 6.0 to about 7.5.

A convenient way of varying the acetonitrile content is by the use of stock solutions and a mixing device for combining the stock solutions in controlled but variable proportions. For example, a combination of two stock liquids may be used, the first being primarily acetonitrile, at least about 75% by volume, preferably 100%, and the second containing all of the other components, including the long chain alkylamine, the quaternary amine, the buffer and the solvent. In preferred embodiments, the alkylamine will be present in the second solution at a concentration of about 0.001% to about 0.05%, the quaternary amine will be present at a concentration of about 0.002M to about 0.05M, and the solvent at about 20% to about 60% by volume, the pH being from about 6.0 to about 7.5. The buffer is preferably within the range of about 0.005 to about 0.1M.

The attached figure is a block diagram illustrating an automated analytical system in accordance with the present invention, as an example embodying the principles described above. The following is a description of this system, including system parameters and operating conditions employed in a prototype constructed in accordance with this system.

The three primary chromatographic columns of the system are contained in a temperature-controlled housing 11 which is maintained at a constant temperature, generally within the range of about 40°-45° C. The three columns are an anion exchange column 12, which contains a packing of styrene-divinylbenzene copolymer with tetramethylammonium functional groups. The average particle size is 11 microns, and the column 10 mm in length and 3.2 mm internal diameter. It is expected that similar columns with lengths up to 30 mm and internal diameter up to 4.6 mm will yield similar results. Downstream of the anion exchange column 12 is the reversed phase column, which is packed with an octyl-bonded silica which has a carbon loading of 9%, an average particle size of about 5 microns and an average pore size of about 120 Angstroms. The column is 20 mm in length and 3.2 mm internal diameter. It is expected that similar results will be obtained by varying the length and diameter within 50%.

The furthest column downstream is the cation exchange column 14, packed with underivatized silica having an average particle size of about 5 microns, an average pore diameter of 50–80 Angstroms, and a surface area exceeding 350 m$^2$/g. The column is 150 mm in length and 4.0 mm in internal diameter, both variable within 20%.

Upstream of these columns is the precolumn 15, of length 15 mm and internal diameter 2.1 mm, packed with a hydrophobic styrene-divinylbenzene packing, with an average particle size ranging from about 12 to about 20 microns.

The system contains a series of liquid reservoirs 18 which supply the various solvents and carrier liquids to the system. Three of the reservoirs 19, 20, 21 feed a common pump 22, while the fourth reservoir 23 feeds a separate pump 24. The separation of feeds between two pumps permits the flow of two different liquid solutions into different portions of the system at the same time. A sample selection valve 25 provides for variable flow selection among the transfer lines leading from the three reservoirs 19, 20, 21 to the pump 22, so that solutions from the three reservoirs can be combined in variable proportions into a single stream. This valve may be incorporated into the pump 22 itself, such as for example a low-pressure ternary gradient pump. The second pump 24 will generally be an isocratic pump.

In the prototype system, the first liquid reservoir 19 contains the application or sample purging buffer. The second and third liquid reservoirs 20, 21 contain liquids which include the components of the carrier solution distributed between them such that, when these liquids are combined in certain proportions, carrier solutions of the desired strengths are obtained. The fourth liquid reservoir 23 contains a fully constituted carrier liquid of a specified strength which can be pumped through the isocratic pump 24 at the same time that a solution drawn from one or more of the first three reservoirs 19, 20, 21 is pumped through the gradient pump 22.

Test samples to be analyzed enter the system through an automated sampling device 28, which draws precisely measured aliquots (0.5 mL) of each test sample and injects them into the flowing liquid stream emerging from the pump 22 at preselected intervals. Conventional equipment designed for serial sample injection is commercially available and may be used.

The arrangement of liquid flows to the various columns, and the connection and disconnection between the columns is achieved by an 8-way valve 30 and two 4-way valves 31, 32. These are conventional pieces of equipment commercially available. Each is shown in one of two positions, the other achieved by rotating in either direction through an arc equal to the distance between adjacent ports. The 8-way valve 1 is arranged to pass fluids through the precolumn 15 in either direction, and to direct the column effluent either to waste 33 or to an input port on the 4-way valve 31 immediately downstream. The latter is likewise arranged to receive fluid streams from the two input lines driven respectively by the two pumps 22, 24, and to direct one of these to the analytical column housing 11 and the other to the second 4-way valve 32 which is interposed between the anion exchange column 12 and the reversed phase column 13. The second 4-way valve 32 in turn receives fluid flow from the anion exchange column 12 and the first 4-way valve 31, and directs one of these to the reversed phase column 13 and the other to waste 34.

The stream emerging from the silica column 14 contains the drugs fully separated and ready for detection. The stream passes through a scanning UV detector 35. This unit consists of conventional instrumentation which detects the peaks as they emerge using standard chromatographic detection methods, and further performs a UV absorptivity scan of each peak preferably at multiple points on the peak, such as the midpoints of the leading and trailing sides as well as the apex of the peak itself. Fluids which have passed through the detector are then passed to waste 36.

The information obtained in the detector 35 is monitored and processed by a computer/monitor unit 37. This unit contains a memory library of retention times and UV absorptivity scans for known drugs, and compares the data received from the detector 35 with the library information as a means of establishing the identity of each drug as it passes through the detector 35. The computer/monitor 37 further integrates the peaks to provide information on the relative amounts of the drugs present in the sample. Thus, for each emerging drug, the system determines its identity (by UV scan and retention time) and its quantity (by peak integration). This information is then transmitted to a printer 38, which provides a full printed analysis of UV-absorbing drugs which have reached the detector.

At the center of the system, coordinating the entire sequence of operations is a system controller 39 which controls the sample selection valve 25, and the computer/monitor 37. The controller 39 computer/monitor 37, printer 38 and detector 35 are conventional equipment commercially available and used in the industry for the same or similar functions.

The following is a sequence of events used for drug analysis of serum or urine on the above described prototype. In this description:

column 1 is the PRP-1 pre-column (element 15 in the drawing)
column 2 is the AMINEX column (element 12)
column 3 is the reversed phase column (element 13)
column 4 is the silica column (element 14)
solvent A is 0.1% borate buffer, pH 8.0 solvent B is a mixture of:
   5 mL 1M KH$_2$PO$_4$
   150 μL dimethyloctylamine
   275 mg tetramethylammonium chloride 645 mL water
   pH adjusted to 6.75±0.02 with H$_3$PO$_4$ or KOH
solvent C is HPLC grade acetonitrile
valve 1 is the 8-way valve (element 30)
valve 2 is the first 4-way valve (element 31)
valve 3 is the second 4-way valve (element 32)

| Duration | Flow Conditions | Event Description |
|---|---|---|
| Step 1 0.5 minute | Column 1 rinsed in 100% C at 4.0 mL/min. Columns 2, 3 and 4 in | Column 1 reactivated to prepare for new |

| Duration | Flow Conditions | Event Description |
|---|---|---|
| | 65% B, 35% C at 1.0 mL/min. Sample pickup in progress. | sample. |
| Step 2 0.5 minute | Column 1 rinsed in 100% A at 4.0 mL/min. Columns 2, 3 and 4 in 65% B, 35% C at 1.0 mL/min. Sample pickup in progress. | Column 1 rinsed with buffer to prepare for new sample. |
| Step 3 0.1 minute | Sample pickup completed. Otherwise same conditions as step 2. | Sample transferred to column 1. |
| Step 4 0.5 minute | Conditions identical to Step 3. | Column 1 rinsed in forward direction. |
| Step 5 1.5 minutes | Valve 1 reversed. Conditions otherwise identical to step 3. | Column 1 rinsed in reverse direction. |
| Step 6 0.2 minute | Valve 2 switched to connect all four columns. 60% B, 40% C at 1.0 mL/min passed through. | High strength mobile phase used to dislodge drugs from column 1. |
| Step 7 0.6 minute | 70% B, 30% C at 1.0 mL/min. | Low strength mobile phase used to continue transfer of drugs, concentrating drugs at heads of analytical columns. |
| Step 8 0.1 minute | 65% B, 35% C at 1.0 mL/min. | Fastest drugs have moved from column 2 to column 3; slowest drugs moving from column 1 to column 2. |
| Step 9 0.5 minute | Valve 2 switched to disconnect columns 1 and 2. 30% B, 70% C passed through column 1 at 1 mL/min; 65% B, 35% C passed through columns 2, 3 and 4 at 1.0 mL/min. | Remaining drugs moving through columns 2 and 3 to column 4. Rinse of column 1 begins. |
| Step 10 5.2 minutes | Valves 2 and 3 switched to connect columns 1 and 2 and disconnect columns 3 and 4. 1 and 2 receive 30% B, 70% C at 1.0 mL/min; 3 and 4 receives 65% B, 35% C at 1.0 mL/min. | All drugs have passed through columns 1 and 2, which are now being rinsed. |
| Step 11 5.2 minutes | 65% B, 35% C passed through columns 1 and 2 at 1.0 mL/min; columns 3 and 4 flow continued as in step 10. | Columns 1 and 2 being reequilibrated in mobile phase. |
| Step 12 .05 minute | All flow rates lowered to 0.1 mL/min. | End of run. |

Note:
Data analysis and printing of the report for each sample occurs during steps 1 through 7 of the subsequent sample.

The following is a representative list of drugs for which a sample of serum or urine may be analyzed by use of the scheme described above. This list is merely illustrative and is not intended to be comprehensive.

DETECTABLE DRUGS

| Drug (in alphabetical order) | Column(s) Where Retained |
|---|---|
| alprazolam | reversed phase |
| amitriptyline | reversed phase, silica |
| amoxapine | reversed phase, silica |
| amphetamine | silica |
| benzoylecgonine | silica |
| butalbital | anion exchange |
| chlordiazepoxide | reversed phase |
| chlorpheniramine | silica |
| cimetidine | silica |
| cocaine | silica |
| codeine | silica |
| desalkylflurazepam | reversed phase |
| desipramine | reversed phase, silica |
| diazepam | reversed phase |
| diphenhydramine | reversed phase, silica |
| doxepin | reversed phase, silica |
| ephedrine | silica |
| ethclorvynol | reversed phase |
| glutethimide | anion exchange |
| imipramine | reversed phase, silica |
| lidocaine | silica |
| lorazepam | reversed phase |
| loxapine | reversed phase, silica |
| maprotiline | reversed phase, silica |
| meperidine | silica |
| methadone | silica |
| methamphetamine | silica |
| methaqualone | reversed phase |
| morphine | silica |
| oxazepam | anion exchange, reversed phase |
| pentazocine | silica |
| phencyclidine | silica |
| phenobarbital | anion exchange |
| phentermine | silica |
| phenylpropanolamine | silica |
| phenytoin | anion exchange, reversed phase |
| propoxyphene | silica |
| pyrilamine | silica |
| quinidine | reversed phase, silica |
| secobarbital | anion exchange |
| thioridazine | reversed phase, silica |
| tripelennamine | silica |

The foregoing is offered primarily for purposes of illustration. It will be readily apparent to those skilled in the art that numerous variations, modifications, and substitutions may be made among the various procedures, materials, and other elements of the system described above without departing from the spirit and scope of the invention.

What is claimed is:

1. A method for analyzing a biological sample for the presence of drugs in the form of anions, bases and neutral compounds, said method comprising:
   (a) purging said sample with a solvent to remove therefrom any inorganic salts and proteins contained therein:
   (b) passing said purged sample obtained in step (a) through the following media in the sequence indicated:
      (i) an anion exchange medium under conditions permitting selective retention of hydrophobic anions and neutral compounds, with substantially no retention of bases;
      (ii) a reversed phase medium under conditions permitting chromatographic separation of weak bases, hydrophobic bases and neutral compounds, with substantially no retention of hydrophilic bases and anions; and
      (iii) a cation exchange medium under conditions permitting chromatographic separation of bases, with substantially no retention of anions; and (c) detecting said drugs in the form of anions, bases and neutral compounds emerging from said cation exchange medium.

2. A method in accordance with claim 1 in which step (b) comprises conveying at least a portion of said purged sample onto said anion exchange and reversed phase media with a first carrier liquid, then passing a second carrier liquid sequentially through said anion exchange, reversed phase and cation exchange media, said first and second carrier liquids both containing acetonitrile, the concentration of said acetonitrile in said first carrier liquid exceeding that in said second carrier liquid.

3. A method in accordance with claim 1 in which said anion exchange medium is a packed column of from about 10 mm to about 30 mm in length, said reversed phase medium is a packed column of from about 10 mm to about 50 mm in length, and said cation exchange medium is a packed column of from about 100 mm to about 250 mm in length.

4. A method in accordance with claim 1 in which said anion exchange medium is a polymeric medium with quaternary ammonium functional sites.

5. A method in accordance with claim 1 in which said anion exchange medium is a styrene-divinylbenzene resin with quaternary ammonium functional sites.

6. A method in accordance with claim 1 in which said anion exchange medium is a styrene-divinylbenzene resin with tetramethylammonium functional sites.

7. A method in accordance with claim 1 in which said reversed phase medium is a derivatized silica.

8. A method in accordance with claim 1 in which said reversed phase medium is silica bearing alkyl functional groups.

9. A method in accordance with claim 1 in which step (a) comprises impregnating a polymeric resin retentive of said drugs with said sample and purging said polymeric resin so impregnated with said solvent to remove said inorganic salts and proteins from said sample.

10. A method in accordance with claim 9 in which said solvent is an aqueous buffer solution at a pH of at least about 7.5.

11. A system in accordance with claim 9 in which said solvent is an aqueous buffer solution at a pH of about 7.5 to about 9.0.

12. A method in accordance with claim 9 in which said polymeric resin is a hydrophobic resin.

13. A method in accordance with claim 9 in which said polymeric resin is a hydrophobic styrene-divinylbenzene copolymer, and said solvent is an aqueous solution of a borate buffer.

14. A method in accordance with claim 13 in which said borate buffer is potassium borate and comprises from about 0.03% to about 0.3% by weight of said aqueous solution.

15. A method in accordance with claim 1 in which step (b) comprises passing a common carrier liquid through each of said media according to said sequence to convey therethrough said purged sample remaining after step (a).

16. A method in accordance with claim 15 in which said common carrier liquid contains acetonitrile at about 10% to about 50% by volume.

17. A method in accordance with claim 16 in which said common carrier liquid further contains dimethyloctylamine at about 30 to about 300 µL per liter.

18. A method in accordance with claim 16 in which said common carrier liquid further contains a member selected from the group consisting of tetraalkylammonium hydroxides and halides at about 0.1 to about 2 g per liter.

19. A method in accordance with claim 1 in which said reversed phase medium is silica bearing alkyl functional groups with a carbon content of about 6% to about 12% by weight.

20. A method in accordance with claim 1 in which said reversed phase medium is silica bonded to a dimethyl alkyl silane in which said alkyl group contains at least 6 carbon atoms and said medium has a carbon content of about 6% to about 12% by weight.

21. A method in accordance with claim 1 in which said reversed phase medium is silica bonded to dimethyl octyl silane with a carbon content of about 8% to about 10% by weight.

22. A method in accordance with claim 1 in which said reversed phase medium is silica bonded to dimethyl octyl silane.

23. A method in accordance with claim 1 in which said cation exchange medium is comprised of underivatized silica.

24. A method in accordance with claim 1 in which said anion exchange medium is a styrene-divinylbenzene resin with quaternary ammonium functional sites, said reversed phase medium is an octyl bonded silica with a carbon content of about 6% to about 12% by weight, and said cation exchange medium is underivatized silica.

25. A method in accordance with claim 1 in which step (a) comprises impregnating an underivatized styrene-divinylbenzene copolymer resin with said sample and purging said resin with an aqueous solution of a borate buffer, and in which said anion exchange medium is a styrene-divinylbenzene resin with quaternary ammonium functional sites, said reversed phase medium is an octyl-bonded silica with a carbon content of about 6% to about 12% by weight, and said cation exchange medium is underivatized silica.

26. A method for analyzing a biological sample for the presence of drugs in the form of anions, bases and neutral compounds, said method comprising:
(a) impregnating an underivatized styrene-divinylbenzene copolymer resin with said sample and purging said sample impregnated on said resin with an aqueous solution of a borate buffer:
(b) passing said purged sample obtained in step (a) through the following media in the sequence indicated:
(i) a column of styrene-divinyl benzene resin with quaternary ammonium functional sites said column ranging from about 10 mm to about 30 mm in length;
(ii) a column of octyl bonded silica with a carbon content of about 6% to about 12% by weight, said column ranging from about 10 mm to about 50 mm in length; and
(iii) an underivatized silica column ranging from about 100 mm to about 250 mm in length;
by way of a carrier liquid containing acetonitrile at about 10% to about 50% by volume, dimethyloctylamine at about 30 to about 300 µL per liter, and a tetraalkylammonium ion at about 0.1 to about 2.0 g per liter, and
(c) detecting said drugs in the form of anions, bases and neutral compounds as they emerge from said underivatized silica column.

* * * * *